(12) United States Patent
Tal et al.

(10) Patent No.: US 10,631,742 B2
(45) Date of Patent: *Apr. 28, 2020

(54) HAND-HELD DEVICE HAVING HEALTH MONITORING CAPABILITIES

(71) Applicant: LIFEWATCH TECHNOLOGIES LTD, Rehovot (IL)

(72) Inventors: Benny Tal, Ashkelon (IL); Yair Tal, Matan (IL); Assaf Pressman, Lehavim (IL)

(73) Assignee: BRAEMAR MANUFACTURING, LLC, Eagan, MN (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/638,479

(22) Filed: Jun. 30, 2017

(65) Prior Publication Data

US 2017/0303804 A1 Oct. 26, 2017

Related U.S. Application Data

(63) Continuation of application No. 13/433,608, filed on Mar. 29, 2012, now Pat. No. 9,693,697.

(51) Int. Cl.
*A61B 5/00* (2006.01)
*A61B 5/024* (2006.01)
*A61B 5/0404* (2006.01)
*A61B 5/0245* (2006.01)
*A61B 5/0452* (2006.01)
*A61B 5/1455* (2006.01)

(52) U.S. Cl.
CPC ........ *A61B 5/02427* (2013.01); *A61B 5/0245* (2013.01); *A61B 5/0404* (2013.01); *A61B 5/0452* (2013.01); *A61B 5/14552* (2013.01); *A61B 2560/0462* (2013.01); *A61B 2560/0468* (2013.01); *A61B 2562/0233* (2013.01); *A61B 2562/046* (2013.01); *A61B 2562/166* (2013.01)

(58) Field of Classification Search
CPC . A61B 5/02427; A61B 5/0404; A61B 5/0452; A61B 5/1455; A61B 5/14551; A61B 5/14552; A61B 5/0245; A61B 5/0205; A61B 5/6825; A61B 5/6826

See application file for complete search history.

(56) References Cited

U.S. PATENT DOCUMENTS 6,330,464 B1 * 12/2001 Colvin, Jr. ........... A61B 5/0031
128/903
6,725,072 B2 * 4/2004 Steuer .................. A61B 5/0261
600/310

(Continued)

*Primary Examiner* — Eric F Winakur
*Assistant Examiner* — Chu Chuan Liu
(74) *Attorney, Agent, or Firm* — Chang B. Hong

(57) ABSTRACT

A method, a computer readable media and a hand-held device, the hand-held device may include a first sensor that is positioned such as to be contacted by a first hand of a user when the user holds the hand-held device; a second sensor that is positioned such as to be contacted by a second hand of the user when the user holds the hand-held device; wherein at least one sensor of the first sensor and the second sensor is a hybrid sensor that comprises an electrode, an illumination element and a light detector; and a health monitoring module arranged to process detections signals from the electrode and from the light detector such as to provide processed signals that are indicative of a state of the user.

25 Claims, 15 Drawing Sheets

(56) References Cited

U.S. PATENT DOCUMENTS

| | | | |
|---|---|---|---|
| 2004/0015091 A1* | 1/2004 | Greenwald | A61B 5/02125 600/513 |
| 2004/0034294 A1* | 2/2004 | Kimball | A61B 5/02125 600/323 |
| 2007/0276262 A1* | 11/2007 | Banet | A61B 5/02255 600/485 |
| 2010/0056880 A1* | 3/2010 | Cho | A61B 5/00 600/301 |

* cited by examiner

HAND-HELD DEVICE HAVING HEALTH MONITORING CAPABILITIES

CROSS-REFERENCE TO RELATED APPLICATIONS

This application is a continuation of U.S. patent application Ser. No. 13/433,608, filed Mar. 29, 2012, which is incorporated herein by reference in its entirety.

BACKGROUND OF THE INVENTION

Modern health monitors are expected to be cheap, reliable and small as possible.

There is a growing need to provide a health monitor that can overcome ambient noises, can operate with low signal to noise ratio and be relatively cheap and compact.

SUMMARY OF THE INVENTION

According to an embodiment of the invention there may be provided a hand-held device that may include (a) a first sensor that may be positioned such as to be contacted by a first hand of a user when the user holds the hand-held device; (b) a second sensor that may be positioned such as to be contacted by a second hand of the user when the user holds the hand-held device. At least one sensor of the first sensor and the second sensor may be a hybrid sensor that comprises an electrode, an illumination element and a light detector. The hand-held device may also include (c) a health monitoring module arranged to process detections signals from the electrodes and from the light detector such as to provide processed signals that are indicative of a state of the user.

The hybrid sensor may include an electrode that defines a light illumination aperture and a light collection aperture. The illumination element may be arranged to direct light towards the user through the light illumination aperture. The light detector may be arranged to detect light from the user that passes through the light collection aperture.

The hybrid sensor may include an electrode that defines a light illumination aperture and multiple light collection apertures. The illumination element may be arranged to direct light towards the user through the light illumination aperture. At least one light detector may be arranged to detect light from the user that passes through the multiple light collection apertures.

The light illumination aperture may be positioned between a pair of light collection apertures.

The at least one light detector may be shielded by an apertured shield.

The hybrid sensor may include multiple illumination elements and multiple light detectors that are spaced apart from each other.

The electrode, the light detector and the illumination element may be proximate to each other. The distance between these elements can be few millimeters, can be smaller than few centimeters, and the like.

The hand-held device may include a third sensor that may be positioned such as to be contacted by the first or second hand of the user when the user holds the hand-held device.

The third sensor may be a hybrid sensor.

The third sensor may be positioned at a first side of the hand-held device while the first and second sensors are positioned at a second side of the hand-held device, the second side may be opposite to the first side.

The third sensor may be positioned such as to be contacted by a thumb of one of the hands of the user while the first and second sensors are positioned such as to be contacted by index fingers of the user.

The hand-held may include a fourth sensor that may be positioned such as to be contacted by the hand of the user that differs from a hand of the user that contacts the third sensor or is the same hand that contacts the third sensor.

The health monitoring module may be arranged to perform a common noise rejection algorithm on detection signals received from electrodes of multiple sensors out of the first, second and third sensors.

The health monitoring module may be arranged to perform the common noise rejection algorithm on detection signals received from electrodes of the first, second and third sensors.

The electrode may include a conductive portion and at least one additional portion.

The additional portion may be nonconductive.

The additional portion may be (for example—at least three times) thicker than the conductive portion. The thickness of the conductive portion can be defined as a thickness of a conductor (such as a conductive plate) that is expected to be contacted by the user.

The health monitoring module may be arranged to process detection signals from the light detector to provide an indication about a blood oxygen saturation level of the user.

The health monitoring module may be arranged to process detection signals from the electrode to provide an indication about an electrical activity of a heart of the user.

The health monitoring module may be arranged to process detection signals from the light detector to provide an indication about an electrical activity of a heart of the user.

The health monitoring module may be arranged to correlate between the detection signals of the light detector and of the electrode to provide an indication about an electrical activity of a heart of the user.

The health monitoring module may be arranged to process the detection signals of the light detector to define a processing window for processing the detection signals of the electrode.

The health monitoring module may be arranged to process the detection signals of the light detector to support the detection of a QRS complex; define an expected timing of a detection of a QRS complex in the detection signals of the electrode; and search for the QRS complex in detection signals of the electrode that are detected in proximity to the expected timing of detection.

The health monitoring module may be arranged to activate the illumination element and the light detector of the hybrid sensor while collecting detection signals from the electrode.

The health monitoring module may be arranged to ignore detection signals from the electrode while measuring a blood oxygen saturation of the user. The blood oxygen saturation can be learnt from a Pulse Plethysmography detected by the health monitoring module.

A method for monitoring a state of a user can be provided. The method may include: (a) receiving detection signals from multiple sensors; wherein the multiple sensors comprise a first sensor that may be positioned such as to be contacted by a first hand of a user when the user holds the hand-held device and a second sensor that may be positioned such as to be contacted by a second hand of the user when the user holds the hand-held device; wherein at least one sensor of the first sensor and the second sensor may be a hybrid sensor that comprises an electrode, an illumination element and a light detector; and (b) processing, by a health monitoring module, the detections signals from at least the electrode and from the light detector such as to provide processed signals that are indicative of a state of the user.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

Figure 1A:
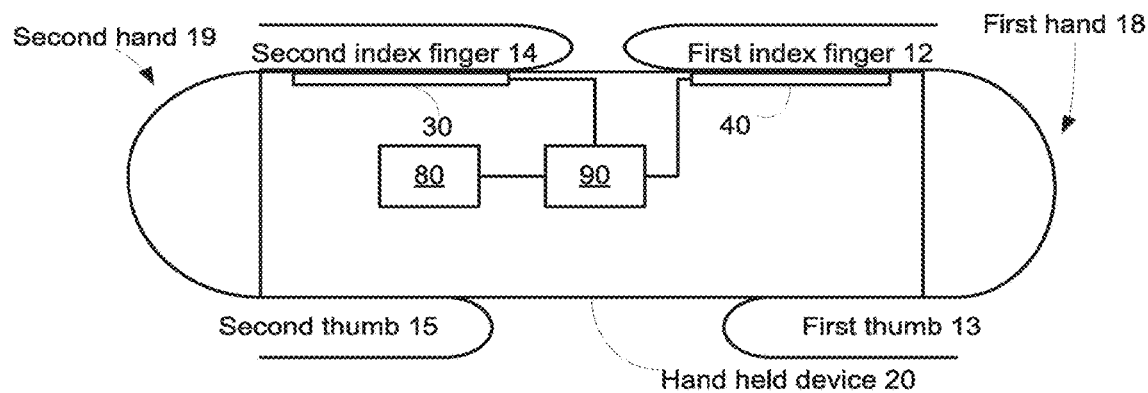
FIGS. 1A-1C illustrate hand-held devices according to various embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The following abbreviations and terms are used in this specification:

| | |
|---|---|
| HR | Heart Rate |
| BE | Backend of a hand-held device. It can be a server which among other tasks runs the algorithm on data which was sent from the hand-held device. |
| QRS | A waveform presented in an ECG during ventricular depolarization |
| RR interval | Distance (time) between sequential QRS complexes - two consecutive R waves |
| PTT | Pulse Transient Time. Time between the occurrence of the QRS complex and the corresponding PPG pulse. |
| Tachycardia | A rapid heart rate, especially one above 100 beats per minute in an adult |

There is provided a compact, cheap and resilient hand-held device that has health monitoring capabilities. The hand-held device can include one or more sensors that are integrated with a smart phone, a media player, a game console, a communication device, a mobile phone, a palm computer and the like.

The device is hand-held in the sense that it can be held by one or two hands of a user. The user can hold the hand-held device with one hand, the device can be attached to a user or to another user accessory but the user can be requested to hold the hand-held device by one or two hands when performing at least one medical examination.

The shape of the hand-held device can be rectangular (as illustrated in FIGS. 1A-1B, 2A-2B and 3A-3B) but can have other shapes such as an oval shape, elliptical shape, a polygon shape and the like.

The hand-held device can include multiple medical sensors that may include electrodes, optical elements, infra-red elements, chemical sensors and the like. One or more of these sensors can be a hybrid sensor that can include different types of sensing elements such as electrodes and light sensing elements.

FIGS. 1A, 1B, 1C, 2A, 2B, 3A and 3C illustrate various examples of hand-held devices 20 that are contacted by users. The following table illustrates the mapping between fingers and sensors (30, 40, 40', 50, 50' 50") that should be contacted by the user, according to various embodiments of the invention.

| | First hand 18 | | Second hand 19 | |
|---|---|---|---|---|
| FIG. | 1st index finger 12 | 1st thumb 13 | 2nd index finger 14 | 2nd thumb 15 |
| 1A | 40 | | 30 | |
| 1B | 40 | 50 | 30 | |
| 1C | | 30 | 50 | 40 |
| 2A | 40 | 50 | 30 | 60 |
| 2B | 40 | 30 | 50, 50' | |
| 3A | 40, 40' | 50, 50', 50" | 30 | 60 |
| 3B | | 30 | 50, 50' | 40 |

FIG. 1A illustrates a hand-held device 20 that is being held by two hands (18 and 19) of a user. The hand-held device 20 may include: (a) a first sensor 40 that is positioned such as to be contacted by a first hand 18 of a user when the user holds the hand-held device 20; (b) a second sensor 30 that is positioned such as to be contacted by a second hand 19 of the user when the user holds the hand-held device; and (c) a health monitoring module 90 arranged to process detections signals from the electrodes and from the light detector such as to provide processed signals that are indicative of a state of the user. The health monitoring module 90 can perform the entire processing, can perform a partial processing and then send (or assist in sending) the partially processed signals to another entity (such as the main processor of the hand held device, a remote processing entity, a medical hub, a hospital etc) to be further processed. The health monitoring module 90 can be dedicated for medical processing or can be also allocated to other tasks. The health monitoring module 90 can be a general purpose processor or a digital signals processor, it can control the functionality of the hand-held device 20.

Either one of the first sensor 40 and the second sensor 30 can be placed on (or embedded with) an edge or a surface of the hand-held device 20 so that once the user touches that edge or surface, the user may touch the first sensor 40.

Figure 1B:
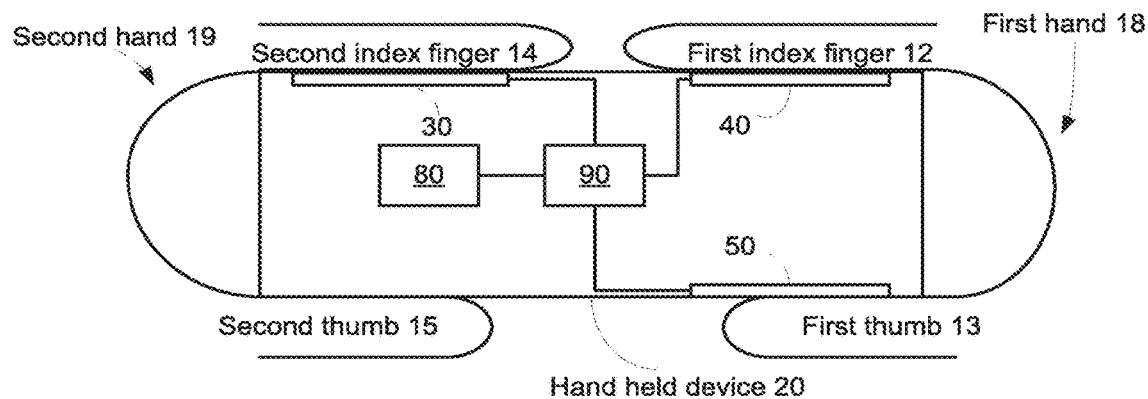
Figure 1C:
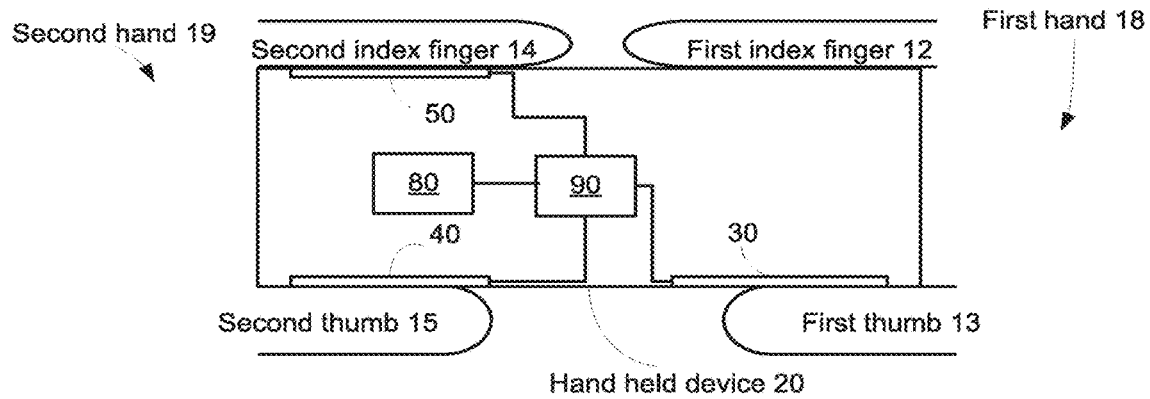

FIGS. 1A and 1B illustrate the first sensor 40 and the second sensor 30 as belonging to a top side of the hand-held device 20 while FIG. 1C illustrates the first sensor 40 and the second sensor 30 as belonging to a bottom side of the hand-held device 20.

The first and second sensors 40 and 30 can be located at the same side of the hand-held device 20, can be positioned at different sides and even opposite sides of the hand-held device 20. For example, first sensor 40 can be positioned at a top side of the hand-held device 20 while the second sensor 30 can be positioned at a bottom side, a sidewall, a back side or even at the front panel of the hand-held device 20.

FIG. 1A also illustrates the hand-held device 20 as including a man machine interface (MMI) element 80. This MMI element 80 can be a screen, a keyboard, a microphone, a loudspeaker, a touch screen and the like. This MMI element 80 can be much bigger than is being illustrated in FIG. 1A. It can span across the entire (or almost entire) hand held device 20. Yet according to another embodiment of the invention one or more sensor is connected to the application processor of the hand held device.

The MMI element 80 can provide to the user instructions to be followed during the medical test. For example, the MMI element can 80 request a user to contact one or more sensors, to limit the movement of the user, to change position or try to clean an electrode if it is detected that a certain electrode does not receive goon enough (too noisy or too weak) signals, and the like. The MMI element 80 can display or otherwise make the user aware of the outcome of the medical evaluation.

At least one sensor out of the first sensor 40 and the second sensor 30 can be a hybrid sensor that may include an electrode, an illumination element and a light detector. Non-limiting examples of a hybrid sensor (denoted 70) are shown in FIGS. 4A-4C and 5A-5C.

According to an embodiment of the invention the hand-held device 20 can include more than two sensors. It can include for example, a third sensor such as third sensor 50 of FIGS. 1B and 1C, 2A, 2*b*, 3A and 3B.

Figure 2A:
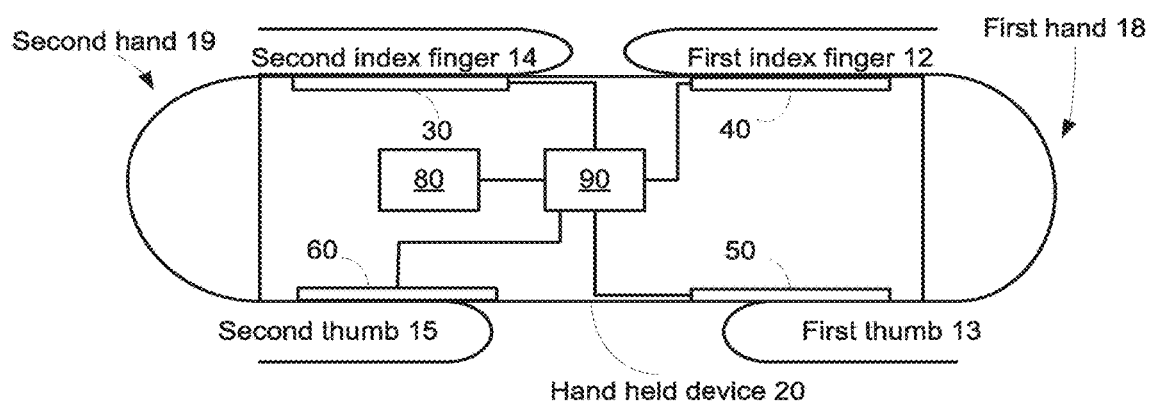
FIGS. 2A-2B illustrate hand-held devices according to various embodiments of the invention.
Figure 2B:
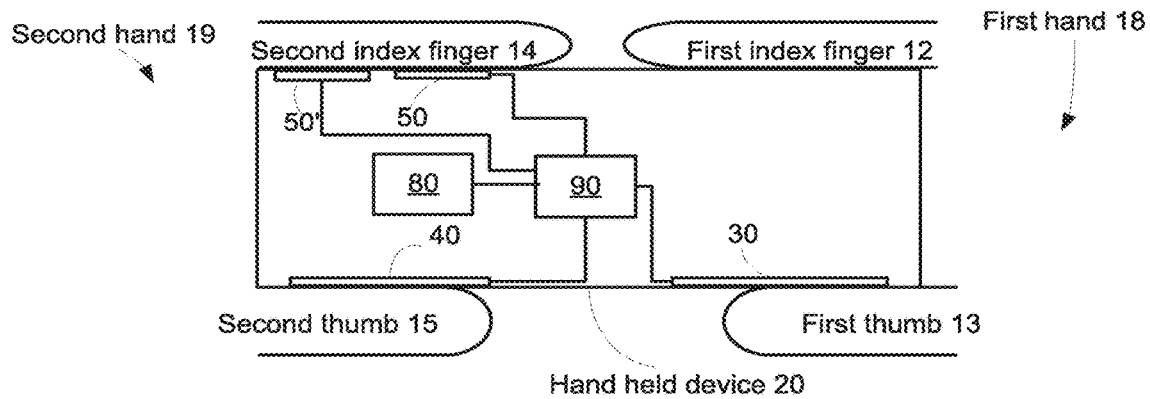
Figure 3A:
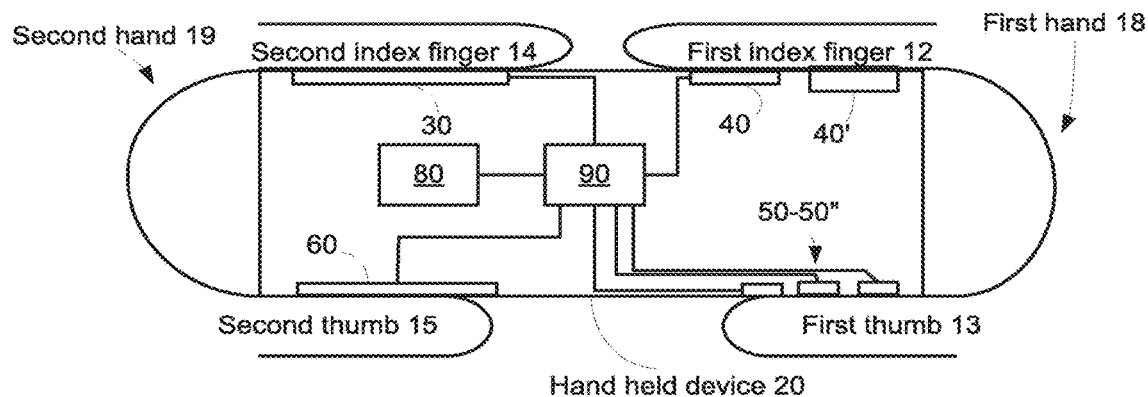
FIGS. 3A-3B illustrate hand-held devices according to various embodiments of the invention.
Figure 3B:
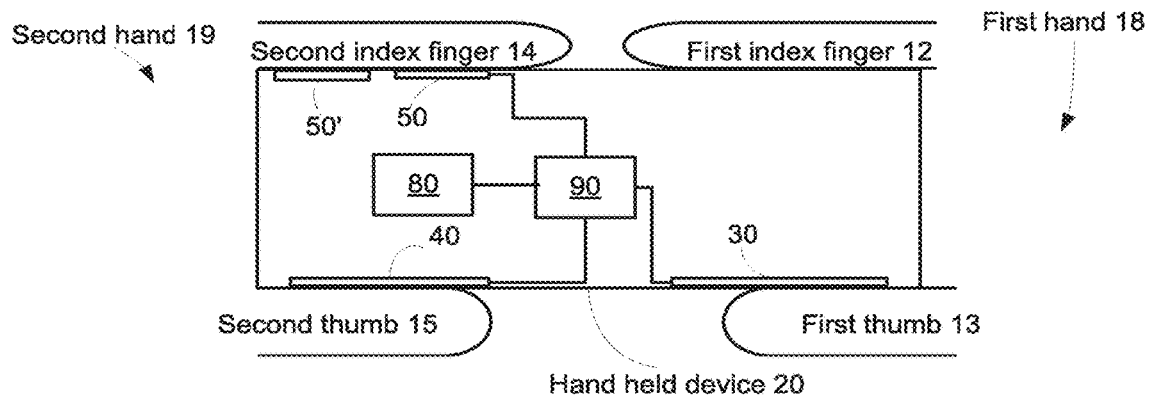

Yet for another example, the hand-held device 20 can include a fourth sensor, such as fourth sensor 60 of FIGS. 2A, 3A and 50' of FIG. 3B.

Yet for a further example, the hand-held device 20 can include a fifth sensor, such as fifth sensor 40' of FIG. 3A, can include a sixth sensor such as sixth sensor 50' of FIG. 3A and can include a seventh sensor such as seventh sensor 50" of FIG. 3A.

The number of sensors of the hand-held device can exceed seven.

The sensors can be positioned such that each sensor is touched by a different finger of the user (as illustrated in FIGS. 1A, 1B, 1C, 2A, 2B) although multiple sensors can be positioned such as to be touched by the same finger of the user (as illustrated in FIGS. 3A and 3B). The number of sensors that can be touched by the same finger can be two, three or more.

Figure 3C:
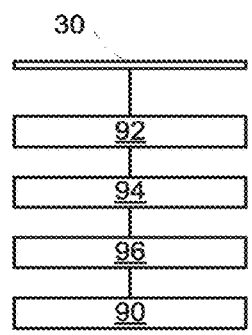
FIG. 3C illustrates a portion of the hand-held device of any of FIGS. 1A-1C, 2A-2B and 3A-3B, according to an embodiment of the invention.

FIG. 3C illustrates a portion of the hand-held device of any of FIGS. 1A-1C, 2A-2B and 3A-3B, according to an embodiment of the invention. FIG. 3A illustrates that a sensor (such as second sensor 30) is coupled to the health processing module 90 via analog circuits such as amplifier 92, mixed signal circuits such as analog to digital converter (ADC) 94 and memory unit 96. Electrical detection signals from an electrode of the second sensor 30 are amplified to amplifier 92 to provide amplified detection signals. The amplified detection signals can converted to digital detection signals that can be stored in memory unit 96 and/or processed by health monitoring module 90.

Figure 4A:
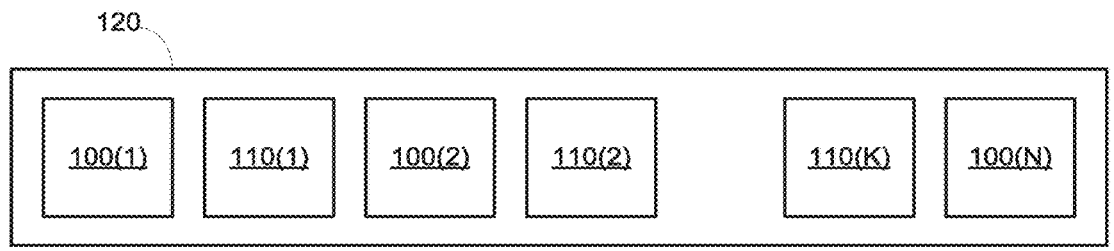
FIGS. 4A-4C illustrate a hybrid sensor according to various embodiments of the invention.
Figure 4B:
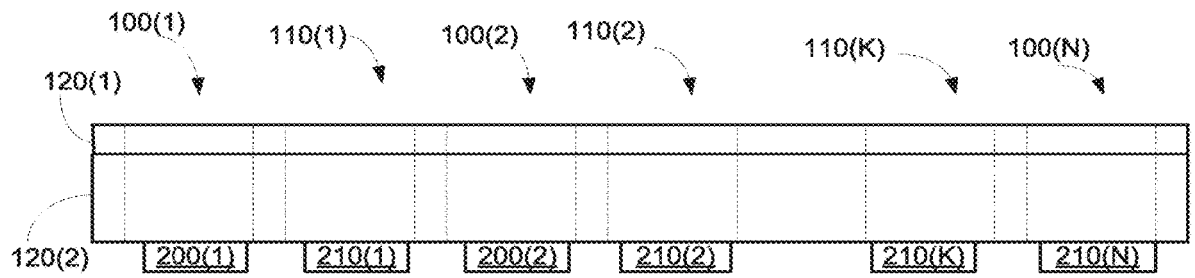

FIGS. 4A and 4B are top and side views of a hybrid sensor 70 according to an embodiment of the invention.

The hybrid sensor 70 includes an electrode 120 that has apertures—light illumination apertures 110(1)-110(K) and light collection apertures 100(1)-100(N). The user, or more specifically a finger of the user that touches the electrode (or is positioned above these apertures) is illuminated by light generated by illumination elements 210(1)-210(K) and directed through the light illumination apertures 110(1)-110(K). Light (scattered and/or reflected) from the finger passes through the light collection apertures 100(1)-100(N) and is detected by light detectors 200(1)-200(N). N and K are positive integers. N may differ from K but N may be equal K.

The electrode 120 is illustrated as including a conductive portion 120(1) that is supported by another portion 120(2).

Figure 4C:
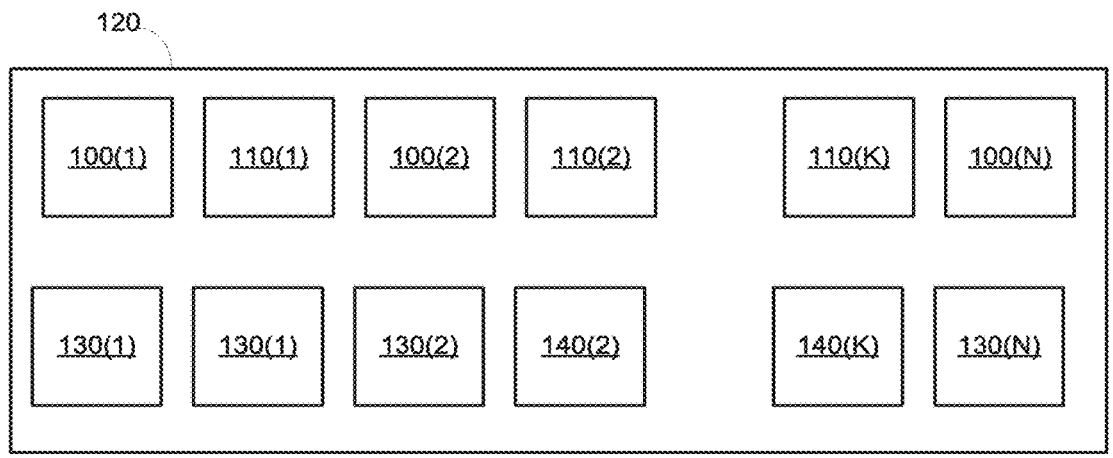

While FIGS. 4A and 4C illustrate a linear array of illumination elements and light detectors it is noted that the light detectors and light detectors can be arranged in other manners—for example, as a rectangular array—as illustrated by the two row array of FIG. 4A.

It is noted that the illumination elements and the light detectors can be arranged in an interleaved manner (as illustrated in FIGS. 4A, 4B, 5A, 5B, and 5C) but can be arranged in other manners.

It is noted that unwanted artifacts and signal noises can be reduced by either one of using electrodes with low impedance, shielding power and signal lines and raising the input impedance of the amplifier.

Figure 5A:
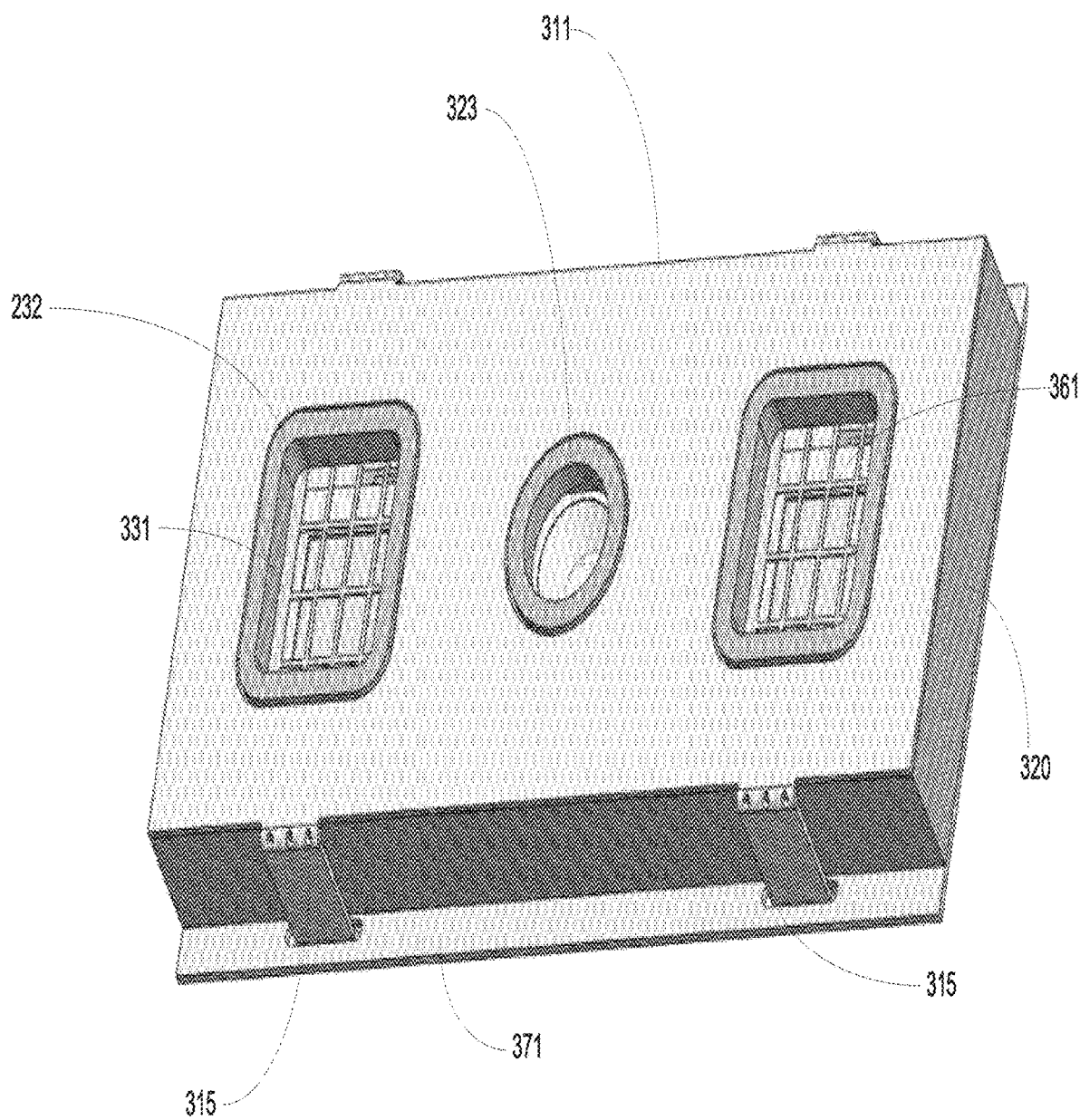
FIGS. 5A-5C illustrate a hybrid sensor according to various embodiments of the invention.
Figure 5B:
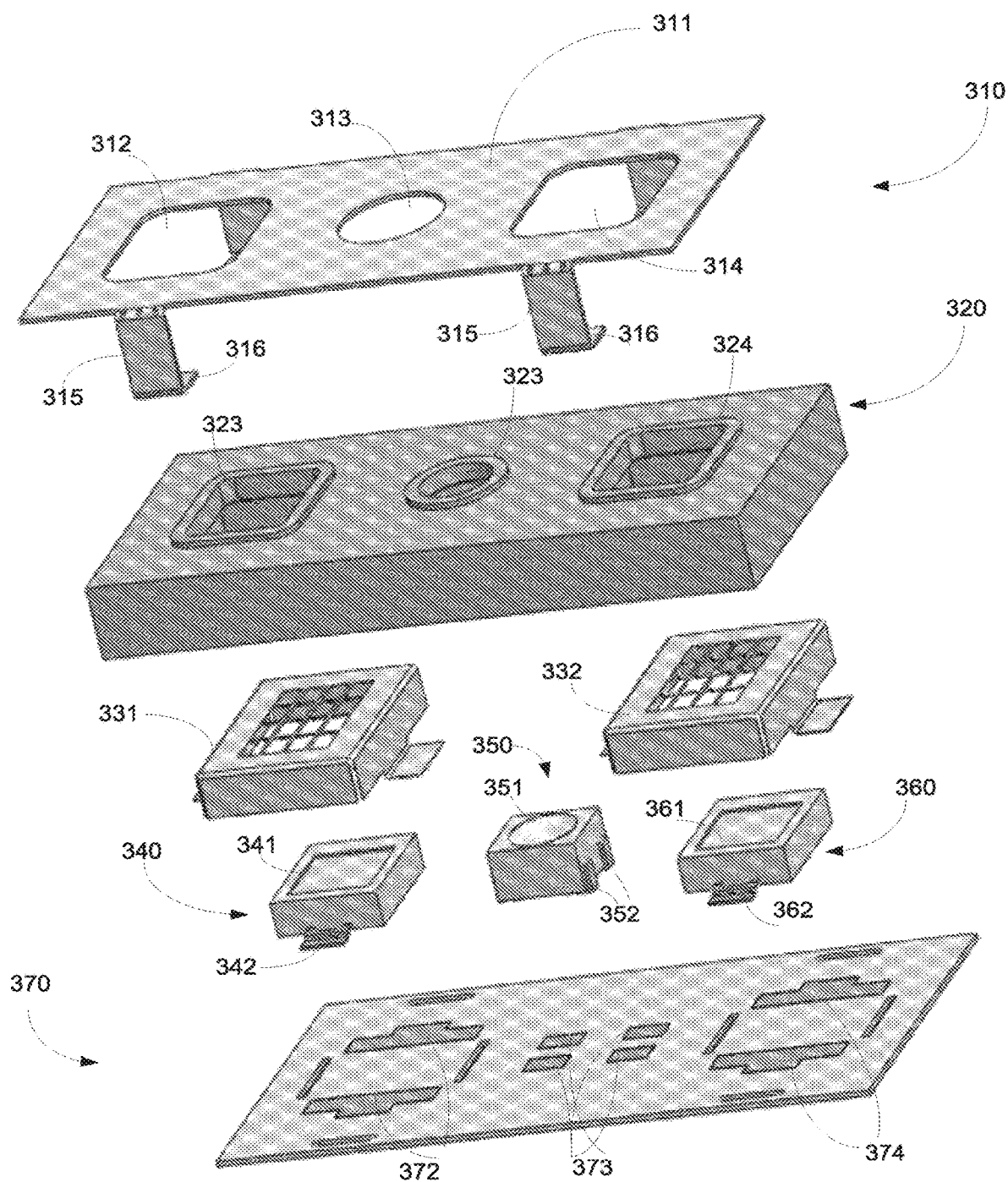
Figure 5C:
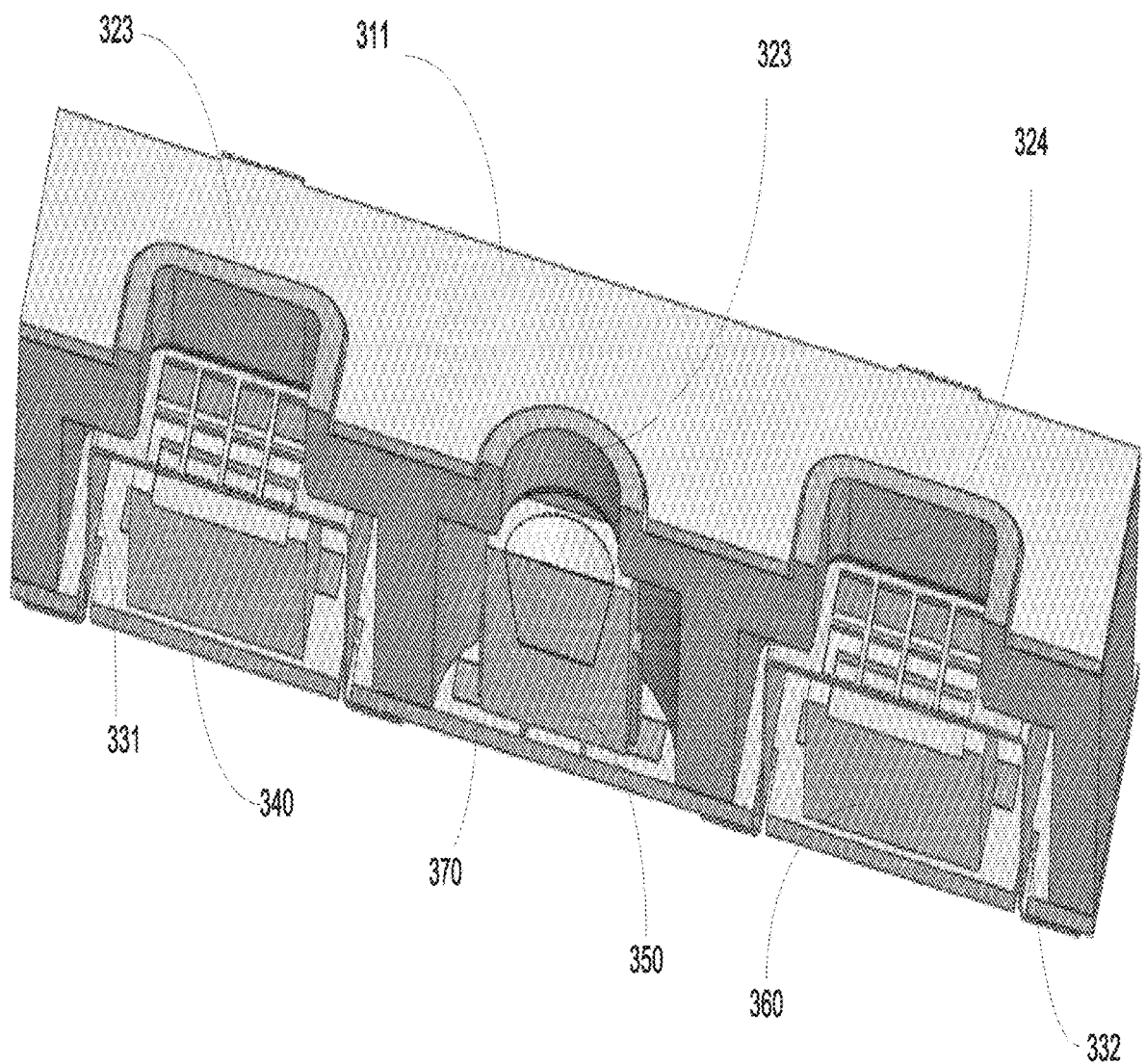

Light from an illumination element can be collected by one or more light detectors. FIGS. 5A-5C illustrate a pair of light detectors per a single illumination element but the ratio can differ from 1:2. If there are more than one illumination elements then the number of light detectors associated with a single illumination element can differ from one illumination element to the other or can be equal to each other.

FIGS. 5A-5C provide a top view, an exploded view and a cross sectional view of a hybrid sensor 70 according to an embodiment of the invention.

The hybrid sensor 70 includes: (a) a conductive portion 310 of an electrode, (b) an additional portion 320 of the electrode, (c) protective shields 331 and 332, (d) illumination element 350, (e) light detectors 340 and 360, and (f) electrical circuit 370.

The electrical circuit 370 can be a rigid or flexible electrical board that provides electrical connectivity (for power supply, control signals and communications) to the illumination element 350 and to light detectors 340 and 360.

The electrical circuit 370 can be connected to a power supply source and to the health monitoring processor.

The conductive portion of the electrode 310 is positioned above other parts of the hybrid sensor 70. It has an upper surface 311 that defines a light illumination aperture 313 that is positioned between two light collection apertures 312 and 314. The upper surface 311 is connected to four supporting legs, each supporting leg is conductive and include a vertical plate 315 and a horizontal plate 316. The horizontal plate 316 can be connected to the board 371 of the electrical circuit 370. The electrical circuit 370 can have slits in which each leg can be inserted to that the horizontal plate 316 can be positioned below the board 317 and can be used for assisting in fastening the elements of the hybrid sensor 70 to each other.

The additional portion 320 of the electrode can provide mechanical support to the conductive portion 310 and can defined spaces (322, 323 and 324) that are positioned below apertures 312, 313 and 314 and allow light to be directed towards the user (through space 323) and be collected (via spaces 322 and 324).

The additional portion can be made of non-conductive material.

Protective shields 331 and 332, and light detectors 340 and 360 can be placed within spaces 322 and 324 while illumination element 350 can be placed within space 323.

Each one of light detectors 340 and 360 and illumination element 350 can conductors (such as 342, 352 and 362) to provide electrical connectivity with conductors (372, 373 and 374) of the board 371.

The hand-held device 20 can activate one sensor or multiple sensors and can correlate or otherwise use detections signals from one sensor to evaluate detection signals from another sensor. For example, the electrode 310 can provide signals that are characterized by a low signal to noise ratio and thus various waveforms such as the QRS complex can be hard to detect. The light detector 350 can sense light that is indicative of a movement of the blood vessels of the user that corresponds to the QRS complex and this detection can be used for defining a time window in which to search for the QRS complex at the signals of the electrode. The time window is time shifted from the appearance of the QRS complex at the light detector signal due to a known delay between the generation of the RQS complex pulse and appearance of a movement that reflects the QRS complex at the hand of the user.

Figure 6:
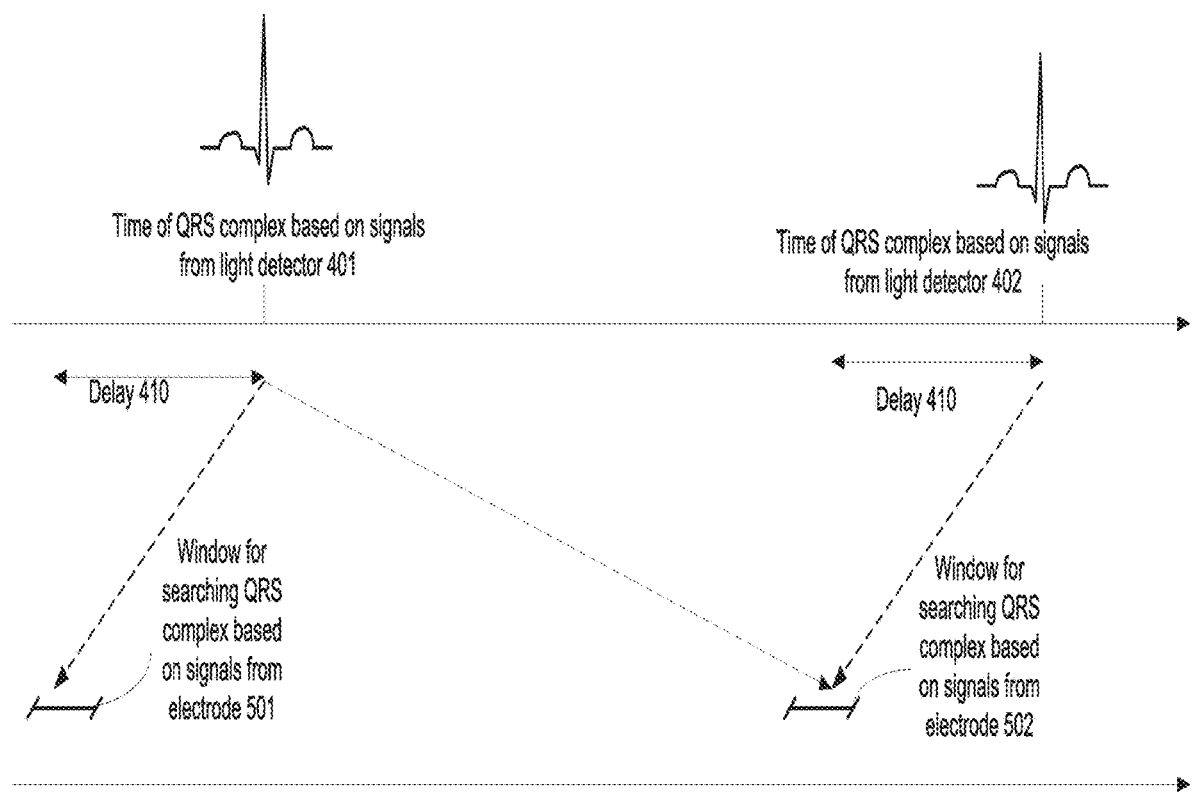
FIG. 6 is a timing diagram according to an embodiment of the invention.

FIG. 6 is a timing diagram according to an embodiment of the invention. The x-axis represents the passage of time.

The health monitoring module receives and processes signals from an electrodes and from a light detector of a hybrid sensor such as hybrid sensor 70.

The health monitoring module detects that at a first point in time 401 a movement of a blood vessel responsive to a QRS complex occurred—based on processing detection signals from the light detectors. The health monitoring module can then define a first window 501 for searching for electrical signals (from the electrode) that represent the QRS complex. The first window 501 precedes first point in time 401 by a known delay that represents an expected timing relationship between a detection of a QRS complex by the electrode and the detection of a movement representative of a QRS complex by the light detector. The health monitoring module can also define a second window 502 base don the first detection (at time 401) and an estimated heart rate of the user or based upon a second point in time 402 in which another movement representative of a QRS complex is detected.

Figure 7:
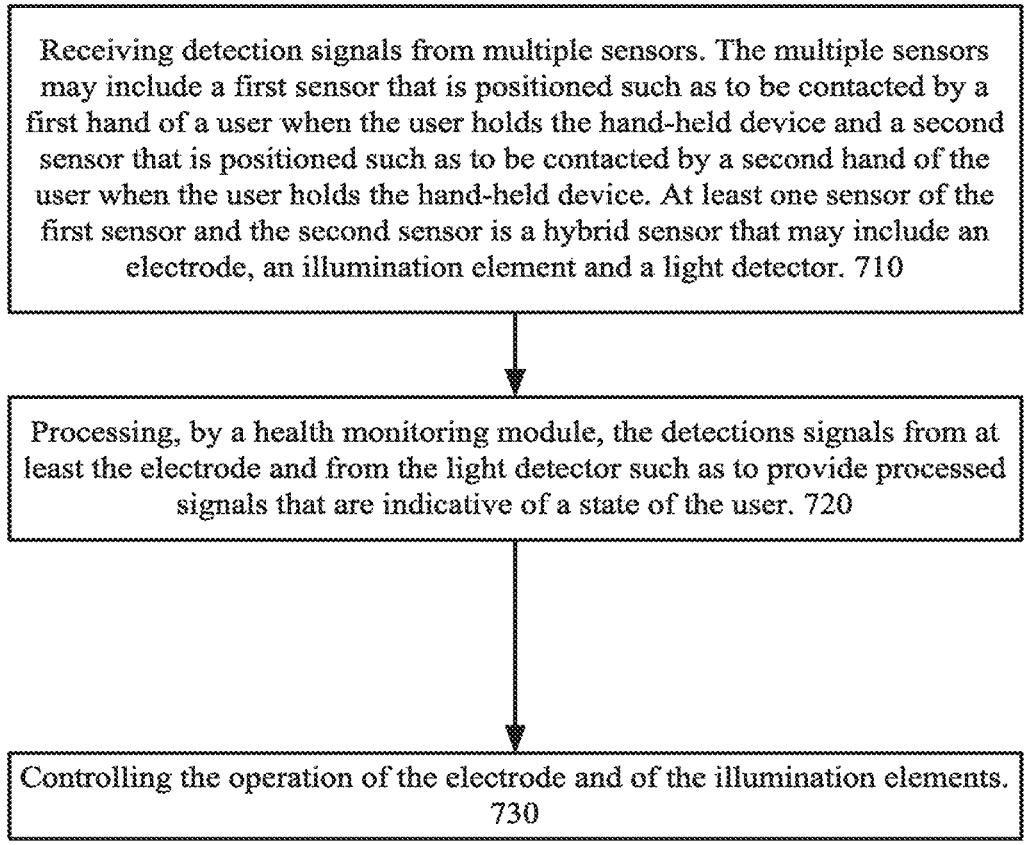
FIG. 7 illustrates a method according to an embodiment of the invention.

FIG. 7 is a flow chart of a method 700 according to an embodiment of the invention.

Method 700 for monitoring a state of a user may start by stage 710 of receiving detection signals from multiple sensors; wherein the multiple sensors comprise a first sensor that is positioned such as to be contacted by a first hand of a user when the user holds the hand-held device and a second sensor that is positioned such as to be contacted by a second hand of the user when the user holds the hand-held device; wherein at least one sensor of the first sensor and the second sensor is a hybrid sensor that comprises an electrode, an illumination element and a light detector.

Stage 710 may be followed by stage 720 of processing, by a health monitoring module, the detections signals from at least the electrode and from the light detector such as to provide processed signals that are indicative of a state of the user.

The hand-held device 20 that executes method 700 can be any of the mentioned above hand-held devices.

For example, stage 710 can include at least one of the following:

1. Receiving detection signals from a hybrid sensor that includes an electrode that defines a light illumination aperture and a light collection aperture; wherein the illumination element is arranged to direct light towards the user through the light illumination aperture; and wherein the light detector is arranged to detect light from the user that passes through the light collection aperture.
2. Receiving detection signals from a hybrid sensor that includes an electrode that defines a light illumination aperture and multiple light collection apertures; wherein the illumination element is arranged to direct light towards the user through the light illumination aperture; and wherein at least one light detector is arranged to detect light from the user that passes through the multiple light collection apertures.
3. Receiving detection signals from a hybrid sensor that includes a light illumination aperture that is positioned between a pair of light collection apertures.
4. Receiving detection signals from a hybrid sensor that includes at least one light detector that is shielded by an apertured shield.
5. Receiving detection signals from a hybrid sensor that includes multiple illumination elements and multiple light detectors that are spaced apart from each other.
6. Receiving detection signals from a hybrid sensor that includes an electrode, a light detector and an illumination element that are proximate to each other.
7. Receiving detection signals from a third sensor that is positioned such as to be contacted by the first or second hand of the user when the user holds the hand-held device. The third sensor can be a hybrid sensor or can differ from a hybrid sensor.
8. Receiving detection signals from a third sensor that is positioned at a first side of the hand-held device while the first and second sensors are positioned at a second side of the hand-held device, the second side is opposite to the first side.
9. Receiving detection signals from a third sensor that is positioned such as to be contacted by a thumb of one of the hands of the user while the first and second sensors are positioned such as to be contacted by index fingers of the user.

10. Receiving detection signals from a fourth sensor that is positioned such as to be contacted by the hand of the user that differs from a hand of the user that contacts the third sensor.
11. Receiving detection signals from a hybrid sensor that includes an electrode that includes a conductive portion and at least one additional portion. The additional portion may be insulating or partially conductive. The additional portion may be thicker (for example—at least three times thicker) than conductive portion.

For example, stage 720 can include at least one of the following:
1. Performing, by the health monitoring module, a common noise rejection algorithm on detection signals received from electrodes of multiple sensors out of the first, second and third sensors.
2. Performing, by the health monitoring module, the common noise rejection algorithm on detection signals received from electrodes of the first, second and third sensors.
3. Processing, by the health monitoring module, detection signals from the light detector to provide an indication about a blood oxygen saturation level of the user.
4. Processing, by the health monitoring module, detection signals from the electrode to provide an indication about an electrical activity of a heart of the user.
5. Processing, by the health monitoring module, detection signals from the light detector to provide an indication about an electrical activity of a heart of the user.
6. Correlating, by the health monitoring module, between the detection signals of the light detector and of the electrode to provide an indication about an electrical activity of a heart of the user.
7. Processing, by the health monitoring module, the detection signals of the light detector to define a processing window for processing the detection signals of the electrode.
8. Processing, by the health monitoring module, the detection signals of the light detector to detect a QRS complex; defining an expected timing of a detection of a QRS complex in the detection signals of the electrode; and searching for the QRS complex in detection signals of the electrode that are detected in proximity to the expected timing of detection.

Method 700 can include stage 730 of controlling the operation of the electrode and of the illumination elements. Stage 730 may include activating the illumination element and the light detector of the hybrid sensor while collecting detection signals from the electrode. Stage 730 may include ignoring detection signals from the electrode while measuring a blood oxygen saturation of the user.

Figure 8:
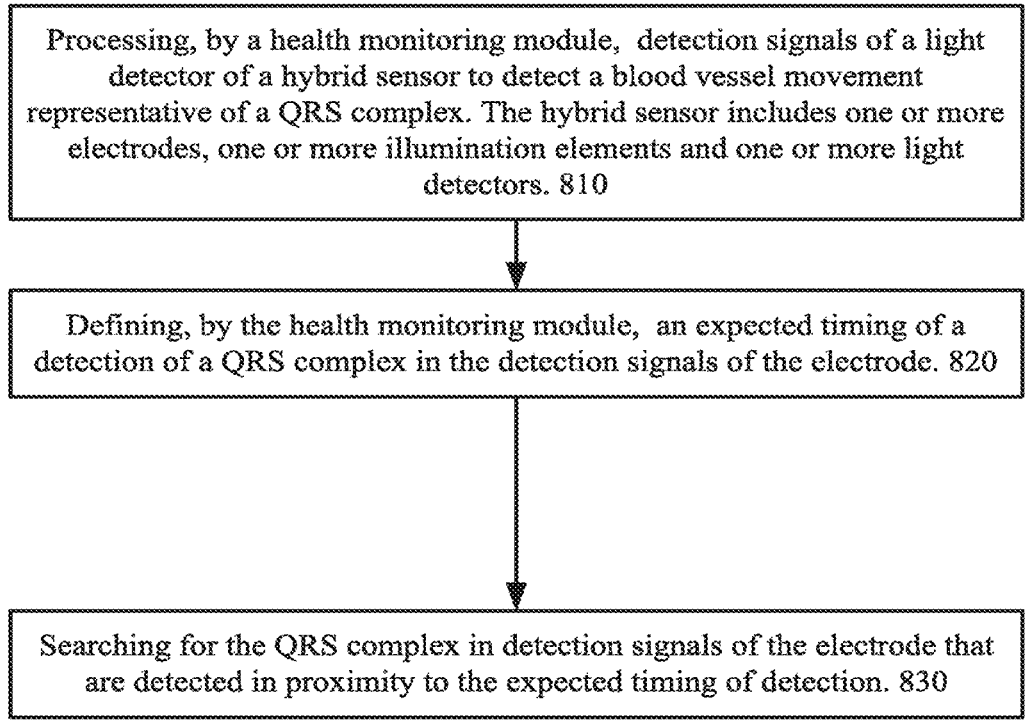
FIG. 8 illustrates a method according to an embodiment of the invention.

FIG. 8 illustrates method 800 according to an embodiment of the invention.

Method 800 may start by stage 810 of processing, by a health monitoring module, detection signals of a light detector of a hybrid sensor to detect a blood vessel movement representative of a QRS complex. The hybrid sensor includes one or more electrodes, one or more illumination elements and one or more light detectors.

Stage 810 is followed by stage 820 of defining, by the health monitoring module, an expected timing of a detection of a QRS complex in the detection signals of the electrode.

Stage 820 may be followed by stage 830 of searching for the QRS complex in detection signals of the electrode that are detected in proximity to the expected timing of detection.

A non-limiting example of an execution of method 800 can be found in FIG. 6.

There is provided a method for monitoring heart related parameters. The method may include detecting QRS complexes on ECG signal, detecting pulsing activities on PPG signals, phase matching and at lease zero optimization stages out of (a) optimal estimation of HR for Bradycardia and Tachycardia detection, and (b) Optimal estimation of HRV for AFIB detection.

The Detection of QRS complexes on ECG signal may include receiving detection signals from one or more electrodes and then differentiating the detection signals in order to get QRS complex slope data.

The following filter can be used to approximate that derivative (Xn, Xn+1 and Xn+2 are samples of the detection signal) $y_n = -x_{n-2} - 2*x_{n-1} + 2*x_{n+1} + x_{n+2}$.

The resultant signal (Yn) is compared to a set of adaptive thresholds to make the final decision (together with the noise detection results).

The detection of pulsing activity on PPG signal may include preprocessing and peak detection.

Figure 9:
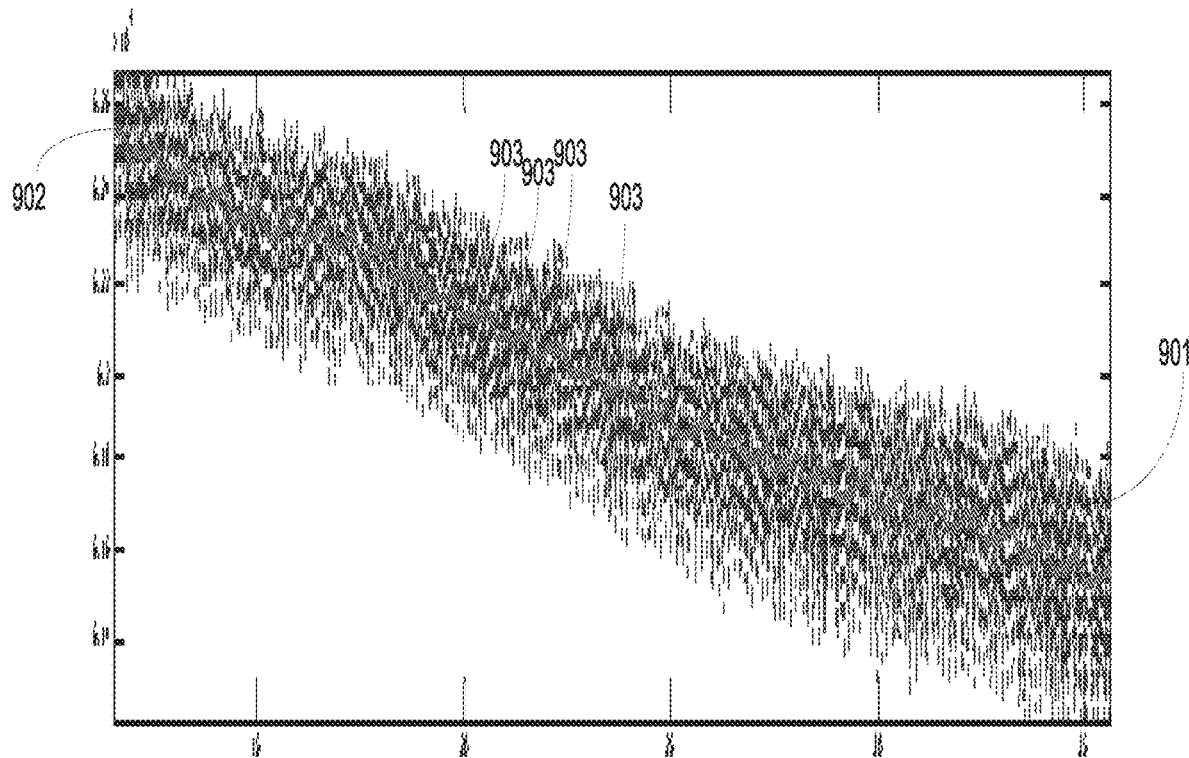
FIG. 9 illustrates a PPG signal and a filtered PPG signal using a finite impulse response filter according to an embodiment of the invention.

The preprocessing may include filtering the PPG signal (for example using a finite impulse response filter with 128 taps between 0.5 and 4 Hz. The outcome of this filtering is a filtered signal. In FIG. 9 the filtered signal is represented by line 902 and the PPG signal is represented by curves 901. The filtered signal 902 shows a pulsing activity where each pulse corresponds to a single heartbeat.

The peak detection includes detecting peaks which correspond to each heartbeat. These peaks are identified by testing whether within each N samples the maximum value appears on sample N/2. N is adjusted so small maxima are not found.

The dots 903 of filtered signal 902 represent some of these peaks. The number of those peaks within a given minute will give the HR in beat per minute (BPM) units.

Two sources of information (PPG pulse timing and QRS pulse timing) both report on the temporal location of the heart contraction and therefore they can be combined and therefore improve the QRS detection. Two problems have to be overcome in order to combine the sources of information: (A) False positive and miss detection of complexes in both the signals and (B) the relative temporal shift between the two sources of information.

Figure 10:
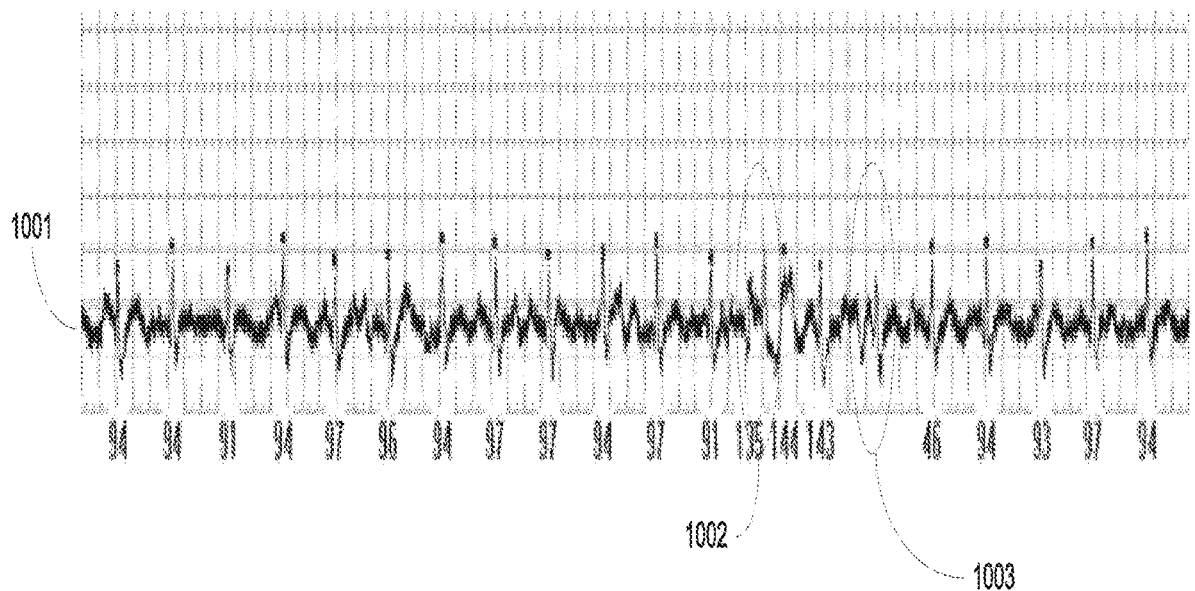
FIG. 10 illustrates an ECG signal according to an embodiment of the invention.

FIG. 10 illustrates an ECG signal 1001. A first ellipse 1002 shows a false detection of a QRS complex. A second ellipse 1003 shows a missed QRS complex.

In FIG. 10 an ECG trace is shown along with beat by beat heart rate (numbers on the bottom of the figure) which are derived by taking the difference in QRS timing. In cases where a QRS is missed and falsely detected the HR which should be around 90 BPM would shift to 144 or 46. The same is true for the PPG signal where complexes might be falsely detected or missed. In order to match between the two sets of detections these false detections and missed complexes should be removed.

False and negative detections may be are removed by fitting a polynomial model (for example—of a third order 3) to the RR sequence.

The RR sequence is generated by taking the difference in time between two consecutive QRS complexes. A missed QRS complex within the sequence will create a large entry whereas a false detection will create a rather small entry into the sequence.

Figure 11:
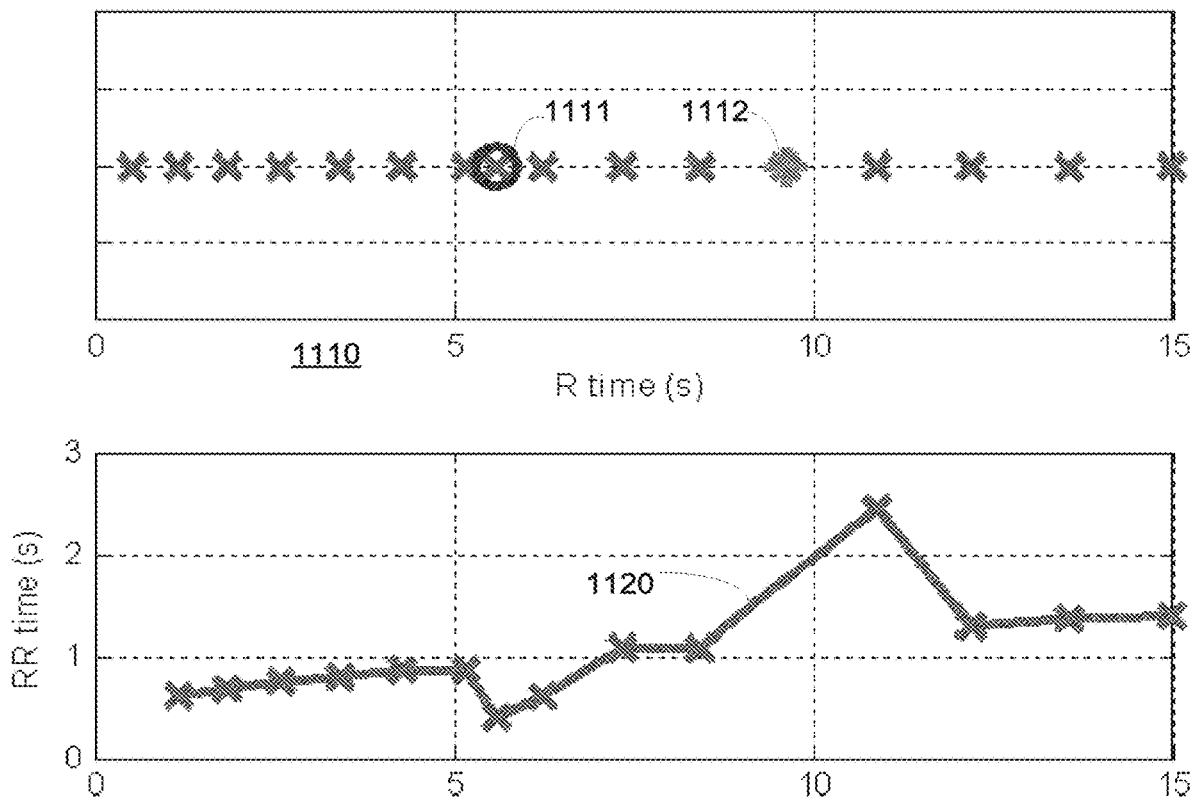
FIG. 11 illustrates a sequence of detection time for QRS complexes according to an embodiment of the invention.

FIG. 11 shows a sequence of detection time for QRS complexes. The top graph 1100 shows the timing of each QRS. The circle 1111 marks a false detection and the magenta asterisk 1112 corresponds to a false detection (the complex was not found).

The bottom graph 1120 shows the RR sequence. It is evident that the false detection (1111) leads to a momentary decrease in RR value. The miss detected QRS complex (1112) led to a large value in the RR sequence.

Once the RR sequence is estimated the method can perform one or more iterations of:
1. Estimating a polynomial model (order 3) to the current RR sequence.
2. Calculating the estimated RR sequence based on the model—call it Err.
3. Calculating an error term e=RR−eRR. In this error term find large entries (lErr) and small entries (sErr). Essentially the lErr terms correspond to missed QRS complexes which result in a high value of RR. The sErr correspond to false detections. And
4. Searching for out layers (lErr and sErr). Remove sErr. Store the lErr.

Stages 1-4 can be repeated until no out layers are found.

Relative temporal shift between PPG and ECG R location.

Figure 12:
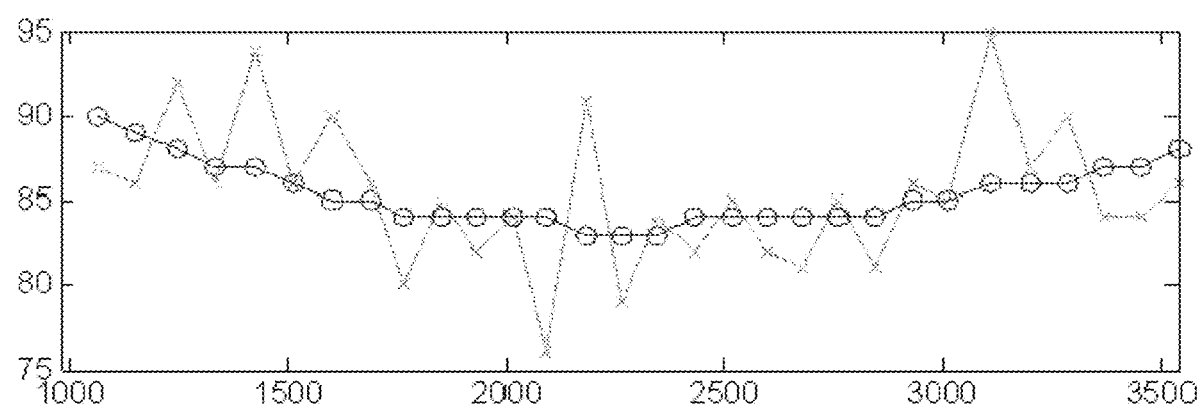
FIG. 12 illustrates an example of a RR sequence and an estimated RR sequence according to an embodiment of the invention.

FIG. 12 illustrates an example of a RR sequence 1201 and an estimated RR sequence (eRR) 1202.

The estimated phase and optimal RR interval can be derived for the remaining sequence of R (after removing lErr and sErr—see above). The optimal RR interval can be $$RR_{opt} = \underset{RR}{\text{argmax}} \left( \text{abs}\left( \sum e^{(j \cdot 2\pi R(n)/RR(n))} \right) \right),$$

$$RR = minRR \ldots maxRR$$

Once the optimal RR value is found ($RR_{opt}$) the angle (or phase) of each R entry can be calculated by:

$$\text{Angle}(n)_{RR} = (2\pi R(n)/RR_{opt})$$

The optimal RR and angle is evaluated or both the QRS complexes and the PPG output.

The two outputs are then compared.

Three ways can be used:
1. Calculating a goodness metric for each measurement, ECG and PPG (usually between 0 to 1) and then combining the two by a weighted sum of the two outputs.
2. Statistical comparison—matching the statistics of $\text{Angle}_{QRS}$ and $\text{Angle}_{PPG}$ by using the Kullback-Leibler divergence.
3. Direct matching—testing the agreement of each entry of one sequence ($\text{Angle}_{PPG}$) with the other ($\text{Angle}_{QRS}$).

Assuming the angle (both PPG and QRS) has a normal distribution the overall agreement between $\text{Angle}_{QRS}$ and $\text{Angle}_{PPG}$ is evaluated by:

$$L_\tau = \prod_i L_i(\text{Angle}(i)_{PPG}, N(\mu_{QRS}, \sigma_{QRS}))$$

Where L is the likelihood function between a single sample (of $\text{Angle}_{PPG}$) in this case and the distribution of $\text{Angle}_{QRS}$.

$$L(X, N(\mu, \sigma)) = \frac{1}{\sqrt{2\pi}\sigma} e^{-\left(\frac{X-\mu}{2\sigma}\right)^2}$$

Figure 13:
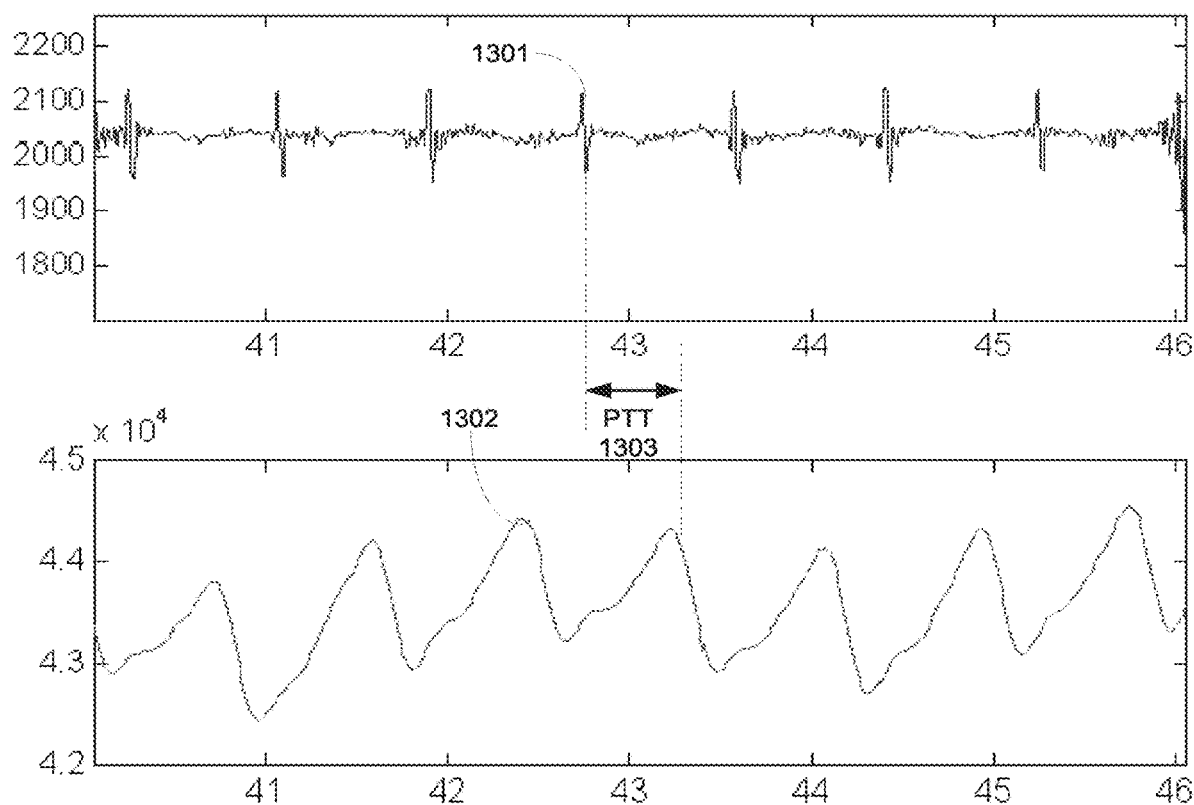
FIG. 13 illustrates an ECG signal and PPG signal according to an embodiment of the invention.

FIG. 13 illustrates the ECG signal 1301, the PPG 1302, as a function of time. It is evident that every ECG QRS complex matches with a peak in the PPG signal. The distance between a peak of the ECG signal 1301 and a adjacent peak of the PPG signal 1302 that follows it represents the pulse transient time (PTT) 1303.

There can be provided a non-transitory computer readable medium that can store instructions for executing any of the mentioned above methods or any combination of any two or more stages of any of the mentioned above methods.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A hand-held device, comprising:
  a first sensor that is configured to be positioned in contact with a first hand of a user when the user holds the hand-held device;
  a second sensor that is configured to be positioned in contact with a second hand of the user when the user holds the hand-held device;
  wherein at least one sensor of the first sensor and the second sensor is a hybrid sensor that comprises an electrode, an illumination element and a light detector; and
  a health monitoring module arranged to process detections signals from the electrode and from the light detector such as to provide processed signals that are indicative of a state of the user by:
  estimating a time interval of a QRS complex from the detection signals of the light detector;
  analyzing the detection signals of the electrode during the estimated time interval; and
  determining the QRS complex at a first time within the estimated time interval based on the analysis of the detection signals.

2. The hand-held device according to claim 1, wherein the electrode of the hybrid sensor defines a light illumination aperture and a light collection aperture; wherein the illumination element is arranged to direct light towards the user through the light illumination aperture; and wherein the light detector is arranged to detect light from the user that passes through the light collection aperture.

3. The hand-held device according to claim 1, wherein the electrode of the hybrid sensor defines a light illumination aperture and multiple light collection apertures; wherein the illumination element is arranged to direct light towards the user through the light illumination aperture; and wherein at least one light detector is arranged to detect light from the user that passes through the multiple light collection apertures.

4. The hand-held device according to claim 3, wherein the light illumination aperture is positioned between a pair of light collection apertures.

5. The hand-held device according to claim 3, wherein at least one light detector is shielded by an apertured shield.

6. The hand-held device according to claim 1, wherein the hybrid sensor comprises multiple illumination elements and multiple light detectors that are spaced apart from each other.

7. The hand-held device according to claim 1, wherein the electrode, the light detector and the illumination element are proximate to each other.

8. The hand-held device according to claim 1, further comprising a third sensor that is configured to be positioned in contact with the first or second hand of the user when the user holds the hand-held device.

9. The hand-held device according to claim 8, wherein the third sensor is a hybrid sensor.

10. The hand-held device according to claim 8, wherein the third sensor is positioned at a first side of the hand-held device while the first and second sensors are positioned at a second side of the hand-held device, the second side is opposite to the first side.

11. The hand-held device according to claim 8, wherein the third sensor is configured to be positioned in contact with a thumb of one of the hands of the user while the first and second sensors are positioned such as to be contacted by index fingers of the user.

12. The hand-held device according to claim 8, further comprising a fourth sensor that is configured to be positioned in contact with the hand of the user that differs from a hand of the user that contacts the third sensor.

13. The hand-held device according to claim 8, wherein the health monitoring module is arranged to perform a common noise rejection algorithm on detection signals received from electrodes of multiple sensors out of the first, second and third sensors.

14. The hand-held device according to claim 13, the health monitoring module is arranged to perform the common noise rejection algorithm on detection signals received from electrodes of the first, second and third sensors.

15. The hand-held device according to claim 1 wherein the electrode comprises a conductive portion and at least one additional portion.

16. The hand-held device according to claim 15, wherein the additional portion is nonconductive.

17. The hand-held device according to claim 15, wherein the additional portion is at least three times thicker than the conductive portion.

18. The hand-held device according to claim 1, wherein the health monitoring module is arranged to process detection signals from the light detector to provide an indication about a blood oxygen saturation level of the user.

19. The hand-held device according to claim 18, wherein the health monitoring module is arranged to process detection signals from the electrode to provide an indication about an electrical activity of a heart of the user.

20. The hand-held device according to claim 1, wherein the health monitoring module is arranged to process detection signals from the light detector to provide an indication about an electrical activity of a heart of the user.

21. The hand-held device according to claim 1, wherein the health monitoring module is arranged to correlate between the detection signals of the light detector and of the electrode to provide an indication about an electrical activity of a heart of the user.

22. The hand-held device according to claim 1, wherein the health monitoring module is arranged to process the detection signals of the light detector to define a processing window for processing the detection signals of the electrode.

23. The hand-held device according to claim 1 wherein the health monitoring module is arranged to activate the illumination element and the light detector of the hybrid sensor while collecting detection signals from the electrode.

24. The hand-held device according to claim 23, wherein the health monitoring module is arranged to ignore detection signals from the electrode while measuring a blood oxygen saturation of the user.

25. A method for monitoring a state of a user, the method comprising:
  receiving detection signals from multiple sensors;
  wherein the multiple sensors comprise a first sensor that is configured to be positioned in contact with a first hand of a user when the user holds the hand-held device and a second sensor that is configured to be positioned in contact with a second hand of the user when the user holds the hand-held device;
  wherein at least one sensor of the first sensor and the second sensor is a hybrid sensor that comprises an electrode, an illumination element and a light detector; and
  processing, by a health monitoring module, the detections signals from at least the electrode and from the light detector such as to provide processed signals that are indicative of a state of the user by:
    estimating a time interval of a QRS complex from the detection signals of the light detector;
    analyzing the detection signals of the electrode during the estimated time interval; and
    determining the QRS complex at a first time within the estimated time interval based on the analysis of the detection signals.

* * * * *